United States Patent [19]
Gagné et al.

[11] Patent Number: 5,989,914
[45] Date of Patent: *Nov. 23, 1999

[54] INTEGRATION CASSETTE FOR IMPROVEMENT OF TRANSGENESIS IN EUKARYOTES

[75] Inventors: Marc Gagné, St-Jean-Chrysostome; Marc-André Sirard, Breakeyville; François Pothier, Saint-Lambert-de-Levy, all of Canada

[73] Assignee: Universite Laval, Quebec, Canada

[*] Notice: This patent issued on a continued prosecution application filed under 37 CFR 1.53(d), and is subject to the twenty year patent term provisions of 35 U.S.C. 154(a)(2).

[21] Appl. No.: 08/656,838

[22] Filed: Jun. 3, 1996

[51] Int. Cl.$^6$ .............................. C12N 15/63; C12N 15/11
[52] U.S. Cl. .................. 435/455; 435/320.1; 536/23.1
[58] Field of Search ................... 536/23.1; 435/172.3, 435/320.1, 455

[56] References Cited

PUBLICATIONS

Thomas et al., 1987, *Cell*, 51:503.
Zimmer et al., 1989, *Nature*, 338:150.
Sambrook et al., 1982, Molecular Cloning: A Laboratory Manual, pp. 1.3–1.100, Cold Spring Harbor Lab., Cold Spring Harbor, N.Y.
Richard et al. Integration of a vector containing a repetitive Line–1 element in the human genome. Molecular and Cellular Biology vol. 14 pp. 6689–6695, 1994.
Zheng et al. Gene targeting in normal and amplified cell lines. Nature vol. 344 pp. 170–173, 1990.
Capecchi Altering the genome by homologous recombination. Science vol. 244 pp. 1288–1292, 1989.
Krimpenfort et al. Generation of transgenic dairy cattle using in vitro embryo production. Biotechnology vol. 9 pp. 844–847, 1991.
Adair et al., 1989, *Proc. Natl. Acad. Sci. USA*, 86;4572.
Brinster et al., 1989, *Proc. Natl. Acad. Sci. USA*, 86:7087.
Gagné et al., 1991, *Mol. Reprod. Dev.*, 29:6.
Gagné et al., 1994, *Transgene*, 1:293.
Smithies et al., 1985, *Nature*, 317:230.

*Primary Examiner*—John S. Brusca
*Attorney, Agent, or Firm*—Birch, Stewart, Kolasch & Birch, LLP

[57] ABSTRACT

The present invention relates to DNA constructs provided to improve transgenesis or genomic integration of DNA fragment of interest into nuclear DNA of eukaryotic cell. The DNA constructs of the present invention allow a more efficient procedure by increasing the rate of genomic integration of a DNA fragment. After integration into host cell's DNA, the DNA constructs may provide a mean of screening transgenic cells. An increasing integration means, as well as a method for screening transgenic cells with said DNA construct are disclosed.

6 Claims, 3 Drawing Sheets

X

|   |   |
|---|---|
| ——— | TARGETED REPEATED GENOMIC SEQUENCE |
| ▭ | HOMOLOGOUS REGION |
| ▭ | GENE OF INTEREST |
| ▭ | PROMOTER |
| X | WHOLE DNA CONSTRUCT OF INTEREST |

―――――― TARGETED REPEATED GENOMIC SEQUENCE
▭▭▭▭ HOMOLOGOUS REGION
▭▭▭▭ PROMOTER

INTEGRATION CASSETTE FOR IMPROVEMENT OF TRANSGENESIS IN EUKARYOTES

BACKGROUND OF THE INVENTION (a) Field of the Invention

The invention relates to a method of transforming eukaryotic cells. More particularly, this invention relates to the use of DNA constructs designed to insert a particular DNA fragment more efficiently into host cell's DNA in the goal of transgenesis.

(b) Description of Prior Art

Using recombinant DNA technology, foreign DNA sequences can be inserted into an organism's genome to alter the phenotype of the host's organism. A variety of different procedures have been described and are utilized to produce stably transformed eukaryotic cells. All of these procedures are based on, first introducing the foreign DNA into the eukaryotic cell, and followed by isolation of those cells containing the foreign DNA into the eukaryotic cell's DNA.

Unfortunately, to produce transgenic animal and plant, all current higher eukaryotic cell transformation procedures produce in very low proportions transformed germinal (oocytes, spermatozoa, zygotes, spermatogonia, blastomers, etc.) or stem cells that contain the introduced foreign DNA inserted throughout the genome. Additionally, the random insertion of introduced DNA into the genome of host cells can be lethal if the foreign DNA happens to insert into, and thus mutate, a unique vital native gene in a critical manner.

Introduction of foreign DNA sequence in the mouse and other laboratory animals is now relatively easy to perform and is currently used in transgenesis. At the moment, progress in adapting the technology to higher plants and animals, particularly to commercially exploited animals (e.g. farm animals), has not reached the integration rate of foreign DNA observed in mice. In mice, transgenesis occurs in about six percent of the zygotes injected, whereas it is only 0.6% in pigs, 0.7% in sheep and 0.5% in cattle.

A technique currently exist for selecting cells after homologous recombination (HR) event between an endogenous gene and a DNA construct carrying a copy of the gene (Smitties et al., 1985, *Nature,* 317:230). This work has been extended for the replacement of a targeted gene or to cause gene deletion as well as introduction of foreign DNA molecules (Thomas et al., 1987, *Cell,* 51:503). In general, one homologous recombination (HR) event occurs for every $10^2$ to $10^5$ non-homologous integration events. The HR approach was also tested for mouse transgenesis by microinjecting the DNA construct directly into the fertilized oocytes (Brinster et al., 1989, *Proc. Natl. Acad. Sci. USA,* 86:7087) The results demonstrated the feasibility of HR to correct a mutant gene which is inactive in fertilized mouse eggs. However, the gene deletion was corrected by HR in one out of five hundred (1/500) transgenic mice that incorporated the injected DNA.

For all the above-mentioned reasons, it would be highly desirable to be provided with a transformation system which would allow integration of a DNA fragment by targeting a repeated site of the host's genome. Preferably, such a system would also provide a means of preventing any insertion into a vital gene or genetic region existing in a single copy.

SUMMARY OF THE INVENTION

One aim of the present invention is to improve the insertion of a length of DNA in the host germinal or embryonic stem cells.

In addition, another aim of the present invention is to provide for a proper selection of the targeted site can minimize position effects, enabling an inserted gene to synthesize an effective amount of its protein product.

Therefore, the present invention allows a much more efficient system of improving the rate of transgenesis in plants and animals than is currently possible.

In accordance with the present invention there is provided a DNA construct for inserting a DNA fragment of interest into eukaryotic host cell, the construct comprising an integration cassette flanked by site-specific recombination sequences in which is inserted the DNA of interest, wherein the DNA fragment of interest is flanked by a nucleotide sequence sharing homology to a nucleotide sequence present in more than one copy in the eukaryotic cell, whereby the integration cassette improve the genomic insertion of the DNA fragment of interest in a site-specific manner.

The DNA sequence of interest may be flanked by nucleotide sequences sharing homology to a repeated nucleotide sequence present in the eukaryotic cell, wherein the flanking nucleotide sequence being linked to only one extremity or to both extremities of a DNA fragment of interest to be integrated into a host cell's genome. Such flanking nucleotide sequences sharing homology with a DNA sequence of the host cell's genome may be selected from the group consisting of a Satellite DNA sequence, corticotropin-β-lipotropin, non-satellite repetitive DNA, histone, ribosomic RNA transfer RNA coding sequences, Pst, Bsu and Alu-like repetitive sequences.

The DNA of interest may be linked to regulatory sequences capable of expressing the said DNA of interest in the eukaryotic cell.

In accordance with the present invention there is also provided a method for improvement of the production of fertile, transgenic eukaryotic organisms wherein the transgenic eukaryotic organisms have a DNA sequence of interest integrated at a predetermined repeated DNA sequence of the organisms, the method comprising the steps of introducing into eukaryotic cells a DNA construct comprising a gene of interest flanked by site-specific recombination sequences, wherein gene of interest is flanked by nucleotide sequences sharing homology to the predetermined nucleotide sequence present in the eukaryotic cell, and the gene of interest is operably linked to regulatory sequences capable of expressing the gene in the eukaryotic cell.

In accordance with the present invention there is also provided a transgenic plant consisting essentially of a plant cell, seed or plant from the in vitro introduction of an exogenous DNA fragment into a plant cell by the method of the present invention.

In accordance with the present invention there is also provided a transgenic animal consisting essentially of an animal cell, gamete, zygote, blastomer, embryonic stem cell or animal from the in vitro introduction of an exogenous DNA fragment into an animal cell by the method of the present invention.

In accordance with the present invention there is also provided a method of directly selecting for insertion of a DNA sequence of interest into a specific sequence of an organism's DNA said method comprising the steps of a) introducing a DNA construct of the present invention into the cells of said organisms;

b) choosing a pair of primers, wherein one primer recognizes a DNA sequences of the DNA fragment of interest, and the other primer recognizes a DNA sequence of the host cell, where the sequence recognized by the other primer exists outside of the DNA construct as described above;

c) using the pair of primers of step b) to amplify the DNA construct inserted into the host cell's genome by homologous recombination; and d) selecting those cells having the DNA construct integrated into the DNA of the cell, thus being transgenic cells.

Additional objects, features, and advantages of the invention will become apparent to those skilled in the art upon consideration of the following detailed description of preferred embodiments exemplifying the best mode of the invention as presently perceived.

DETAILED DESCRIPTION OF THE INVENTION

Figure 1A:
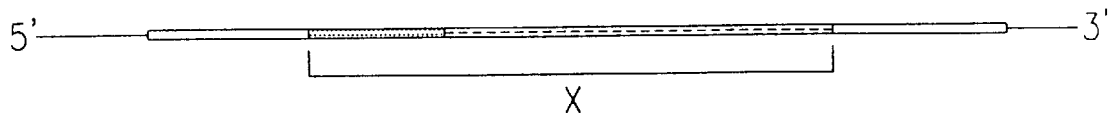
FIG. 1 illustrates a schematic representation of DNA constructs in accordance with the present invention, respectively with both extremities repeatedly, invertedly or partially homologous, 5' homologous and 3' homologous.

In accordance with one preferred embodiment of the present invention, the transformation of eukaryotic cells is improved by the use of DNA sequences that are identical to a repeated predetermined sequence to the eukaryote's DNA. Typically the introduced DNA sequence will constitute entire functional genes.

Here eukaryotic cells includes all manipulated gametes, zygotes, embryos, blastomers or embryonic stem cells used to create a transgenic organism. Eukaryotic cells can also be transformed with other DNA sequences such as gene transcription and translation regulatory sequences. Transcription and translation regulatory sequences are those DNA sequences necessary for efficient expression of a gene product. In general such regulatory elements can be operably linked to any gene to control the gene's expression, the entire unit being referred to as the "expression cassette". An expression cassette is intended to typically contain, in addition to the coding sequence, a promoter region, a translation initiation site and a translation termination sequence. Selected endonuclease restriction sites may also be included at the ends of an expression cassette to allow the cassette to be easily inserted or removed when creating DNA constructs.

The expression of a gene is primarily directed by its own promoter, although other DNA regulatory elements are necessary for efficient expression of a gene product. Promoter sequence elements include the TATA box consensus sequence (TATAAT), which is usually 20 to 30 base pairs (bp) upstream of the transcription start site. In most instances the TATA box is required for accurate transcription initiation.

Promoters can be either constitutive or inducible. A constitutive promoter controls transcription of a gene at a constant rate during the life of a cell, whereas an inducible promoter's activity fluctuates as determined by the presence (or the absence) of a specific inducer. The regulatory elements of an inducible promoter are usually located further upstream of the transcriptional start site than the TATA box. Ideally, for experimental purposes in accordance with the present invention, an inducible promoter should possess each of the following properties: a low to non-existent basal level of expression in the absence of inducer, a high level of expression in the presence of inducer, and an induction scheme that does not otherwise alter the physiology of the cell. The basal transcriptional activity of all promoters can be increased by the presence of an "enhancer" sequence. Although the mechanism is unclear, certain defined enhancer regulatory sequences are known, to those familiar with the art, to increase a promoter's transcription rate when the sequence is brought in proximity to the promoter.

The creation of a transformed cell requires that the DNA be physically placed within the host cell. Current transformation procedures utilize a variety of techniques to introduce DNA into a cell. In one form of transformation, the DNA is microinjected directly into cells through the use of micropipettes. Alternatively, high velocity ballistics can be used to propel small DNA associated particles into the cell. In another form, the cell is permeabilized by the presence of polyethylene glycol, thus allowing DNA to enter the cell through diffusion. DNA can also be introduced into a cell by fusing protoplasts with there entities which contain DNA. These entities include minicells, cells, lysosomes or other fusible lipid-surfaced bodies.

Transformed cells, those containing the DNA inserted into the host cell's DNA, can be selected from untransformed cells if a selectable marker is included as part of the introduced DNA sequences. Selectable markers include genes that provide antibiotic resistance (e.g. G418) or herbicide (e.g. kanamycin, hygromycin) resistance. Alternatively, conventional techniques like restriction enzyme digestion and Southern blot are generally used for the molecular analysis of events such as HR. However, in certain cases where genomic DNA of transformed cells is available in very low quantities, analysis by these conventional methods can make selection of transgenic cells unperformable. Amplification of targeted DNA sequence by polymerase chain reaction (PCR) allows detection in a sensitive and highly selective manner of this DNA fragment. PCR is an alternative method which has been used to reveal HR events in eukaryotic cells (Zimmer et al., 1989, Nature, 338:150). HR analysis by PCR which gives a desired response is an indication that introduced DNA construct is integrated in the targeted sequence of the host cell's DNA. All the transformation techniques described above have the limitation that they result in rare inserted copies, and result in foreign DNA insertions in very small number or cells, most particularly in gametes and zygotes. Therefore the proportions of transgenic organisms is low too.

The present invention enables the increase of integration of a foreign DNA fragment in the host cell's genome, while it allows to the targeting of a length of DNA to a specific repeated site. Presumably the selected targeted site will also allow the inserted gene to produce its protein production an amount sufficient to produce the desired effect.

In one preferred embodiment, the introduced DNA consists of combination in tandem arrangement of a promoter region linked to a gene or interest flanked by partial of total half-cutted or repeated DNA fragments homologous to a sequences existing in the host cell's DNA. The length of the homologous fragments can vary from 2 to 10 thousands base pairs (bp).

The first element of the invention involves the use of a DNA fragment identical to a specific repeated site in the host cell's genome to flank the DNA costruct to introduce. Targeting can be carried out via homologous recombination. Homologous recombination is a reaction between any pair of DNA sequences having a similar sequence of nucleotides (homologous sequences, where the two sequences interact (recombine) to form a new recombinant DNA species. The frequency of homologous recombination increases as the number of copies and the length of the shared nucleotide DNA sequence increases, and is higher with linearized plasmid molecules than with circularized plasmid molecules. Homologous recombination can occur between two DNA sequences that are less than identical, but the recombination frequency declines as the divergence between the two sequences increases.

Introduced DNA sequences may be targeted via homologous recombination by linking the DNA of interest to sequences sharing homology with endogenous sequences of the host cell. Once the DNA enters the cell, the two homologous sequences can interact to insert the introduced DNA at the site where the homologous genomic DNA sequences were located. Therefore, the choice of homologous sequences that contain the introduced DNA will determine the rate and site at which the introduced DNA is integrated. For example, in the goal to produce transgenic animals, if the DNA of interest is linked to DNA sequences sharing homology to a single copy gene of the host eukaryotic cell, the DNA sequence of interest may be inserted via homologous recombination in a very low proportion of manipulated cells. However, if the DNA sequence of interest is linked to DNA sequences sharing homology to a multi-copy DNA sequence of the host eukaryotic cell, then the DNA sequence of interest can be inserted in many specific sites where a copy of the genomic DNA sequence is located. Preferably, the predetermined host DNA site of insertion is a non-essential endogenous gene or other genomic DNA sequence present in high copy number, such as a DNA satellite sequence. Alternatively, the homologous region flanking the gene(s) of interest could exists in only two copies in the host cells DNA.

DNA can be inserted into the genome by a homologous recombination reaction involving either a single reciprocal recombination (resulting in the insertion of the entire length of the introduced DNA) or through a double reciprocal recombination (resulting in the insertion of only the DNA located between the two recombination events). A single homologous recombination event may then result in the entire introduced DNA sequence being inserted into the genomic gene. Alternatively, a double recombination event can be achieved by flanking each end of the DNA sequence of interest (the sequence intended to be inserted into the genome) with DNA sequences homologous to the targeted genomic sequences. Although introduced sequences can be targeted for insertion a specific genomic site via homologous recombination, in higher eukatyotes, homologous recombination is a relatively rare event compared to random insertion events. In plant cells, foreign DNA molecules find homologous sequences in the cell's genome and recombine at a frequency of 0.5 to $4.2 \times 10^{-4}$ (the number of targeted events divided by the number of random integration events), while in animal one homologous recombination occurs against $10^2$ to $10^5$ random recombinations. Thus the efficiency or production of transgenic plant or animal can be potentially increased by flanking a transgene with repeated host cell's DNA sequences.

One way to control the activity of the transgene product is to link it to an inducible promoter. Inducible promoters include any promoter capable of increasing the amount of gene product produced, by a given gene, in response to exposure to an inducer. Inducible promoters are known to those familiar with the art and a variety exist that could conceivably be used to drive expression of the transgene.

Two preferred inducible promoters are the heat shock promoter and the glucocorticoid system. Promoters regulated by heat shock, such as the promoter normally associated with the gene encoding the 70-kDa heat shock protein, can increase expression several-fold after exposure to elevated temperatures. The heat shock promoter could be used as an environmentally inducible promoter for controlling transcription. The system consists of a gene encoding glucocorticoid receptor protein (GR) which in the presence of a steroid hormone forms a complex with the hormone. This complex then binds to a short nucleotide sequence (26bp) named the glucocorticoid response element (GRE), and this binding activates the expression of linked genes.

Figure 1B:
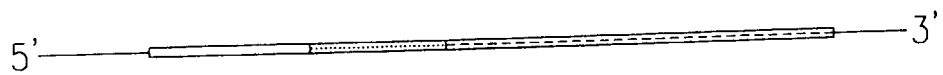
Figure 1C:

As shown in FIG. 1, the transformation construct can also include a polylinker region located in the genomic DNA sequence. The addition of a polylinker region promotes the ease of constructing unique DNA molecules. Through the use of specific nucleotide restriction enzymes, gene cassettes and other DNA sequences can be inserted into the polylinker region. Any DNA sequence inserted into the polylinker can then be flanked with identical sequences of the host genome to improve insertion into a host cell's DNA via site specific recombination. Typically all the genes contained on the introduced DNA will be linked to a regulatory sequences capable of expression the gene's product in a eukaryotic cell.

As shown in FIG. 1, constructs can be physically linked to additional sequences to form a circularized DNA molecule (a plasmid). These additional sequences would contain a gene's cassette encoding a bacterial selectable marker and a bacterial origin of replication. This plasmid is useful in generation large amounts of the DNA constructs. The procedure consists of using this plasmid to transform bacterial cells, growing the bacterial cells under selection for the presence of the plasmid and then finally isolating the plasmid from the replicated bacterial cells. In order to prevent integration of unnecessary plasmid DNA that is outside the site-specific recombination sequences, the plasmid will also contain restriction endonuclease sites that allow the removal of the plasmid sequences prior to transformation.

The present invention will be more readily understood by referring to the following example which is given to illustrate the invention rather than to limit its scope.

EXAMPLE I

Recombination of Foreign DNA with Homologous Terminating Ends Following Microinjection into Bovine Embryos The annealing pathway of homologous recombination (HR) appears to be functional in a number of higher eukaryotic systems, including mammalian embryos. In accordance with this Example, the efficiency of the process in fertilized bovine oocytes was studied. The possibility of improving HR transgene incorporation reported by Brinster and colleagues was examined (1989, *Proc. Natl. Acad. Sci. USA*, 86:7087) in flanking the 3' only or both ends of the foreign marker DNA with halves of a bovine Satellite DNA. This centromeric sequence was estimated as existing in at least a thousand copies in the genome. A high frequency of recombination during the S phase was observed in centromeric regions of Drosophila genomes.

Gene targeting in the bovine satellite DNA sequences was performed by microinjection in interphasic zygotes (Gagné et al., 1995, *Mol. Reprod. Dev.*, 41:184–194) for the following reasons: 1) to improve transgenesis' efficiency in bovine species, 2) to prevent mosaisism resulting from transgenes introduced by microinjection into eggs that are not usually represented in the germ line of the first generation: 3) to drive the integration of foreign DNA in such a way to control the influence of the regions around the integration site and to prevent the alteration of a vital gene by insertion: 4) to allow selection of embryos showing site specific integration by the PCR technique before transfer into recipient cows.

Preparation of Bovine Oocytes

Bovine ovaries were obtained from a local slaughterhouse. Cumulus-oocyte complexes were aspirated from antral follicles (1–5 mm in diameter) with a hypodermic needle (18 G), selected for a compact and complete cumulus, and then washed three times in tyrode-Hepes medium supplemented with 3 mg/ml fatty acid free bovine serum albumin (BSA), 0.2 mM pyruvate, 50 µg/ml gentamicin, 5 mM glucose, and pH adjusted to 7.4 before use.

Oocyte Maturation (IVM) and Fertilization (IVF)

Maturation of groups of 10 cumulus-enclosed oocytes per 50 µl drop of culture medium was carried out in 60-mm petri dishes for 25 h at 38.5° C. in 5% $CO_2$ and air with water-saturated atmosphere. Oocyte maturation medium consisted of TCM 199 supplemented with 10% heat-treated fetal calf serum (FCS: Gibco Lab, NY), 2.2 mg/ml $NaHCO_3$, 5 µg/ml of oLH, NIADDK (National Institute of Diabetes and Digestive and Kidney Diseases), 0.5 µg/ml NIADDK oFSH-17, 1 µg/ml estradiol-17β (Sigma Co, MO), 0.2 mM pyruvate, and 50 µg/ml gentamicin. In vitro fertilization was carried out as follows. Two µl of swim-up-separated semen was added to the oil-covered fertilization drops containing five matured oocytes for a final concentration of $1 \times 10^6$ cells/ml. Fertilization medium consisted of tyrode lactate medium supplemented with 0.6% BSA, 0.2 mM pyruvate, 2 µg/ml heparin, and 50 µg/ml gentamicin. Fertilization was performed at 38.5° C. in 5% $CO_2$ in water-saturated atmosphere. The same procedure can be applied to in vivo matured oocytes or alternatively zygotes can be obtained after fertilization in vivo.

DNA Constructs and Microinjection

Figure 2A:
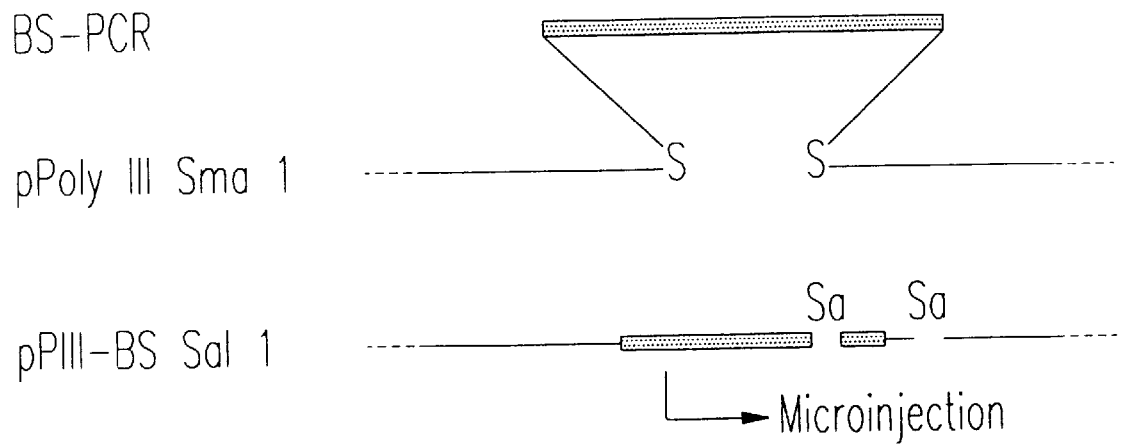
FIG. 2 illustrates the synthesis of the constructs in accordance with the present invention.
Figure 2B:
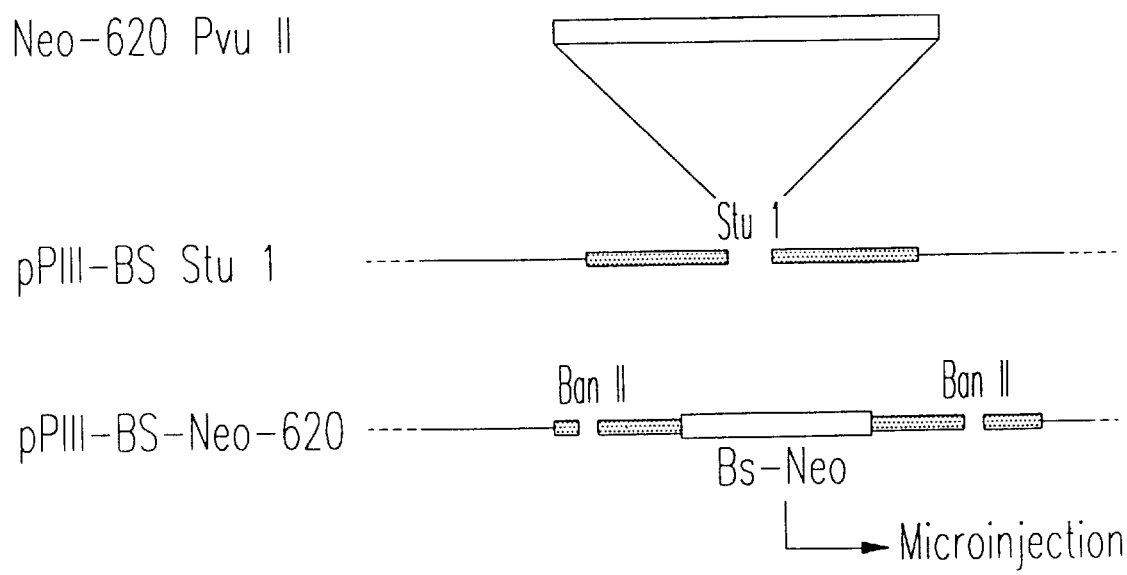

Construction were performed according to standard DNA recombination procedures (Maniatis et al., 1982, *Molecular Cloning*, Cold Spring Harbor). FIG. 2 illustrates the construct synthesis, where PCR amplified bovine satellite sequence (1.3 kb) was integrated in a Sma I (S) digested pPoly III vector (2.1 kb). A Sal I (Sa) fragment (215 bp) was removed from the plasmid pPIII-BS(3.5 kb), and the resulting Sal I pPIII-BS (3.285 kb) was directly injected as one-sided homologous DNA. For the other construct, a Pvu II (P) fragment of the $Neo^r$ gene (620 bp) was ligated to the Stu I (St) cleaved pPIII-BS. The fragment BS-Neo (1.54 kb) was obtained by digestion of the plasmid pPIII-BS-Neo-620 with Ban II (B).

Figure 3:
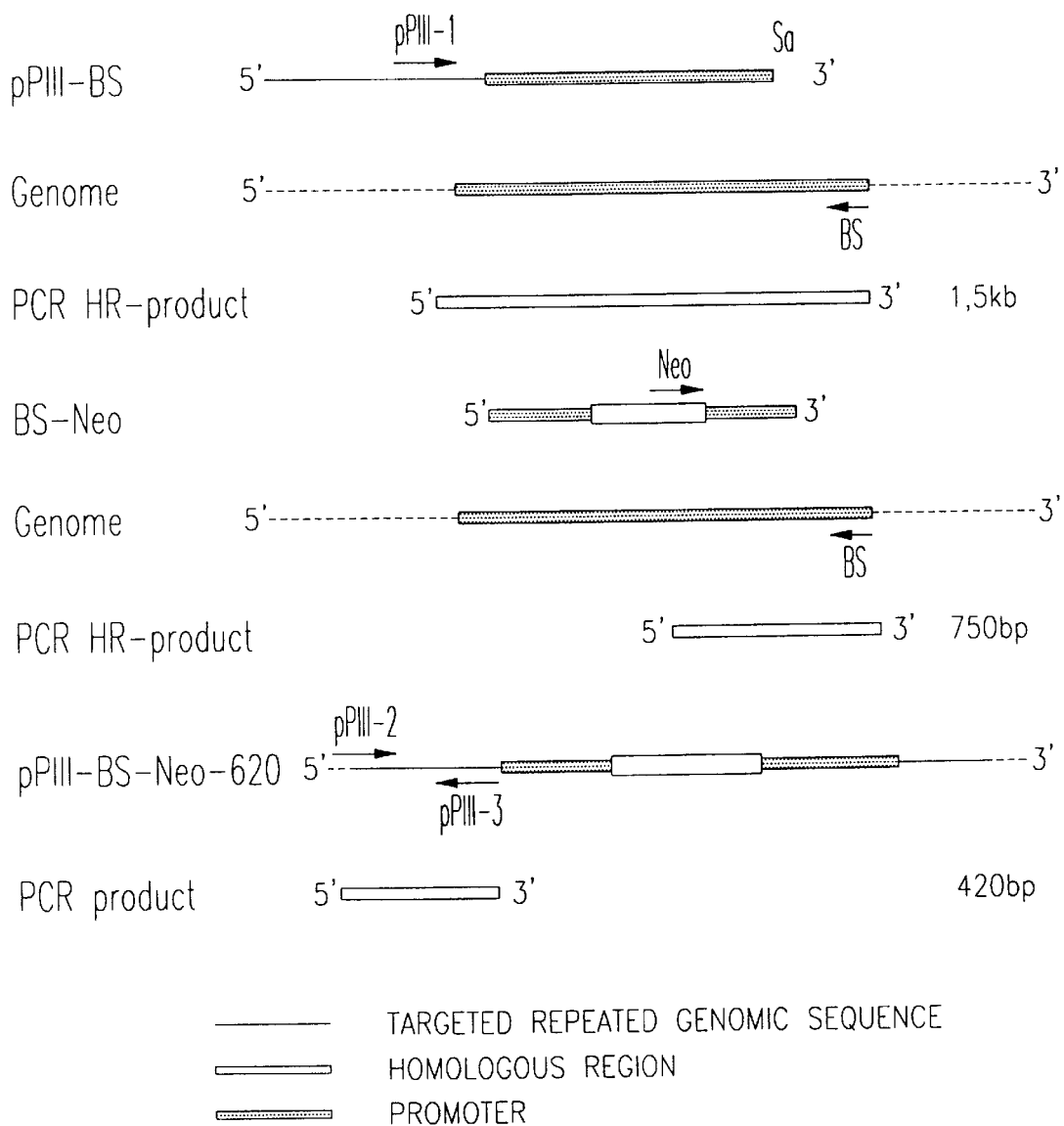
FIG. 3 illustrates the recognition sites of the oligonucleotide primers used in the PCR reactions in accordance with the present invention.

Bovine satellite sequences (BS) were used as the homologous region. Bovine genomic DNA was extracted, purified and the 1.3 kb BS sequence was amplified by PCR. Oligonucleotide primers are shown in FIG. 3. The PCR product was electrophoresized on a 1% agarose gel, and extracted from the gel by electrodialysis. The amplified BS sequence was introduced in the plasmid vector pPoly III (2.1 kb) digested at the Sma I site located in the polylinker. The resulting pPIII-BS plasmid vector (3.4 kb) was opened in the BS sequence at the unique Stu I site (near the center of the sequence), or at the Sal I site (located at the 3' end of the BS sequence). The Sal I cleaved pPIII-BS plasmid was used directly for microinjection. A segment of 620 bp of the $Neo^r$ gene (Neo-620) was isolated from the plasmid pMCl-Neo (Stratagene, La Jolla, Calif., USA) by digestion with restriction enzyme Pvu II. The Pvu II Neo-620 fragment was than ligated with the Stu I digested pPIII-BS plasmid. The BS-Neo fragment (1.532 kb) was finally excised from the pPIII-BS-Neo-620 construct by digestion with Ban II. The linearized Sal I pPIII-BS and the BS-Neo fragment were injected into one of the bovine oocytes pronuclei between 17 and 19 h post-insemination (hpi). This timing was chosen because this is the point at which the chromatin replication process is at its maximum rate and the embryos are most resistant to microinjection (Gagné et al., 1995, *Mol. Reprod. Dev.*, 41:184–194). DNA fragments were injected at concentrations of 0.1, 0.5, 1.0 and 2.0 ng/µl, diluted in a $T_{10}E_{0.5}$ (Tris 10 mM, EDTA 0.5 mM, pH 7.4) buffer. It was verified whether this plasmid had any effect on the normal development of embryos by comparing with results of injection of the pRGH-527 plasmid which does not contain homologous regions at 2 ng/µl.

In Vitro Development and Culture of Embryos

In vitro development of embryos took place in 50 µl drops of TCM-199, supplemented with 10% FCS, 0.2 mM pyruvate, and 50 µg/ml gentamicin, under oil, at 38.5° C., 5% $CO_2$, and air with a water saturated atmosphere. Embryos were co-cultured with bovine epithelial oviductal cells as described before (Gagné at al., 1991, *Mol. Reprod. Dev.*, 29:6). Culture medium was replenished after 2 days by adding 50 µl of fresh medium. After 5 days of culture, the development of embryos was assessed on the basis of morphological criteria.

DNA Amplification

After 5 days of culture, whole embryos were extracted from zona pellucida by dissection with a 25 G needle in PBS ($Ca^{2+}$-$Mg^{2+}$ free), washed once taking care of changing the pipette at each manipulation. The embryonic cells were placed in a 100 µl sterile reaction mixture consisting of 10 mM Tris-HCl, pH 8.3, 50 mM KCl, 1.5 mM $MgCl_2$ and 20 mM of each deoxynucleotide. For the first amplification, a set of primers (FIGS. 2–3) was chosen to detect the homologous recombination. For the pPIII-BS plasmid (one side homology), one primer started at the 3' end of the pPIII sequence (oligo pPIII-1), and in the case of the BS-Neo fragment (two sides homology), one primer started at the 3' end of the Neo sequence (oligo Neo), and the complementary primer for both amplifications started at the 3' end of the genomic BS sequence (oligo BS). A control set of primers was used to identify the genomic DNA by amplifying a 320 bp targeted sequence of the Kappa-casein gene (oligos kappa 1 and 2). A second amplification set to detect the presence of the complete pPIII-BS-Neo-620 or uncleaved pPIII-BS plasmids (which could allow amplification and thus give a false HR positive response) was carried out on 10 ul of each resulting PCR product. Amplification with primers pPIII-2 and -3 should give a band of 420 bp on the gel if one of the plasmids is present in the samples.

Oligonucleotide primer sequences:

PIII-1 (SEQ ID NO:1)
   5=-GGGTATCACGAGGCCGGAT-3' pPIII-2 (SEQ ID NO:2) 5'-GGCACCTATCTCAGCGAT-3' pPIII-3 (SEQ ID NO:3) 5'-GGAGGACCGAAGGAGCT-3'

Neo (SEQ ID NO:4)
   5'-CCGCCTGGGTGGAGAGGCTATT-3'

BS (SEQ ID NO:5)
   5'-CCGTCATCGCAAGATGAAGCCCT-3'

KC-1 (SEQ ID NO:6)
5'-CCTGCCCAAATTCCTCAATGG-3'
KC-2 (SEQ ID NO:7)
5'CTGCGTTGTCTTCTTTGATGTC-3'

The complete plasmid pPIII-BS-Neo-620 was used to determine the appropriate amplification conditions. Before adding 2.5 units of Taq DNA polymerase (Perkin-Elmer Cetus), the samples were heated for 10 min at 100° C. The solution was covered with 100 µl of mineral oil, and amplification was carried out using a Perkin-Elmer Cetus thermal cycler. The procedure consisted of 40 cycles of denaturation at 93° C. for 30 sec., annealing at 59° C. for 30 s and extension at 72° C. for 90 sec. To avoid false-positive detections, which result mainly from contamination of the sample with the final amplification product, we used several measures including physical isolation of the PCR preparation from the final products and use of positive displacement pipettes (Gilson, Villiers-Le-Bel France). Following amplification, 20 µl of each sample were submitted to electrophoresis on a 1% agarose gel. Statistical analysis was carried out by Chi-square test.

Effects of Microinjected Constructs pPIII-BS and BS-Neo on the In Vitro Development of Embryos Linearized pPoly III plasmid vectors were injected in 18 hpi bovine oocytes. They were flanked at the 3' end by a 1.3 kb bovine satellite (BS) sequence, and a 620 bp fragment of the Neo gene flanked at each side respectively by 5' and 3' halves of the BS sequences. A group of untreated zygotes was kept as control and a group was injected with the Bgl II linearized plasmid pRGH-527 as foreign DNA without homologous sequences (nHS). From the present experiments, we observed that injection of the nHS plasmid significantly affected ($p<0.005$) embryo development: 12% (n=53) of treated embryos and 23% (n=278) of controls developed to morula stage (>16 cells). Surprisingly, when injected foreign DNA was flanked by homologous sequences on one or both sides, embryo development was even more impaired. Zygotes in which 0.1, 0.5, 1.0 and 2.0 ng/µl of pPIII-BS (one-sided homology) were injected reached the morula stage in proportions of 9% (n=77), 6% (n=116), 4% (n=95), and 1% (n=75) respectively. Embryos in which BS-Neo (two-sided homology) was injected, have developed to morula stage in proportions of 11% (n=92), 4% (n=104), 6% (n=104), and 0% (n=88) respectively. The harmful effects of homologous sequences on embryo development was significantly higher ($p<0.01$) at concentrations as low as 0.5 ng/µl than in nHS pRGH-527 plasmid at concentrations of 2 ng/µl.

Evidence of Genomic Insertion with One-Side and Bilateral Homologous Transgene

The basic strategy used here was to select primers such that amplification could occur only when homologous recombination had taken place. As illustrated in FIG. 3, primers pPIII-1 and Neo were chosen from the region unique to the injected constructs and primer BS from genomic DNA sequence in the targeted gene but outside of the region used for the HR constructs. Amplification products should be produced only when a construct carrying homologous extremities has been incorporated in its chromosomal homologous sequence and the primers pPIII-1 and Neo sequences have thus been integrated in continuity with the primer BS genomic sequence; no exponential amplification products should appear when the HR constructs have failed to be integrated or have been integrated at a random genomic site.

If integration of injected pPIII-BS and BS-Neo DNA had occurred at the homologous genomic sequences, we should have detect the 1.5 kb and 750 bp fragments respectively on the agarose gels. The genomic control kappa-casein (KC) primers should give a fragment of 320 bp. PCR assay to detect the one-sided HR was performed on 11 embryos developed beyond the 12-cell stage. Of the 11 embryos tested, 3 were found PCR positive for the HR event because of the presence of the 1.5 kb product. When homologous sequences were presented at both sides of the foreign DNA, which was the case for the BS-Neo fragment, the 750 bp band specific to HR was detected in 12 embryos (lanes 3, 5, 6, 9, 10, 11, 14, 17, 18, 22, 23 and 26) out of 26 developed beyond the 12-cell stage.

We are well aware that positive PCR response for HR of injected DNA could be due to the presence of uncleaved and contaminant plasmid constructs, which before digestion contain the annealing sequence of the primer BS, and might allow amplification of the targeted HR sequences. Further analysis was conducted on the PCR reaction mixture following amplification to identify whether the PCR HR-products were due to a contaminating whole plasmid. Amplification was performed with primers pPIII-2 and -3 specific to a pPolyIII region (420 bp). A band of 320 bp specific to the KC gene was present in all samples, including uninjected embryos, but not in the negative and plasmid controls, thus indicating that genomic DNA from embryos was present. However, the targeted sequence of pPolyIII was not detected in 10 of the 12 PCR samples that were HR-positive from the previous amplification. In the other two samples, some weak unspecific bands were observed, including one at 420 bp.

Conclusion

Conventional techniques like restriction enzyme digestion and Southern blot are generally used for the molecular analysis of events such as HR. However, it was previously observed (Gagné et al., 1991, *Mol. Reprod. Dev.,* 29:6) that there is not enough genomic DNA in a single bovine embryo to perform these methods. In addition, it was not possible to use the expression of a foreign gene as a recombination marker since it was also observed (Gagné et al., 1994, *Transgene,* 1:293) that the transcription of the *E coli* lacZ gene driven by the 5' flanking region of the chicken β-actin gene could be supported by embryonic cells without being integrated. PCR is an alternative method which has been used to reveal HR events in eukaryotic cells (Zimmer and Gruss, 1989, *Nature,* 338:150).

Current recombination models require the presence of homology between two DNA sequences on both sides of a recombining site to initiate a recombination reaction. The observation that the frequency of DNA integration is increased by addition of homologous sequence on one side in mammalian cells (Adair et al., 1989, *Proc. Natl. Acad. Sci. USA,* 86:4572) supports our results. In the case of the two-sided homologous construct, 38 percent of embryos retained (beyond the 12-cell stage) enabled amplification of the 750 bp fragment used to identify the HR event.

In conclusion, the molecular approach is critical in attempts to produce transgenic domestic animals. The data presented here supports that transgenesis via homologous recombination by using a highly repeated genomic sequence is possible in bovine embryos. The results demonstrates that transgenesis efficiency by homologous recombination is potentially high. Once embryonic cells are increasingly transformed by homologous recombination with repeated sequences, they can be selected by PCR to know if the inserted DNA fragment is integrated to the genome.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

We claim:

1. A method of insertion of a DNA sequence of interest into a predetermined naturally occurring repeated genomic DNA sequence of a cultured eukaryotic host zygote comprising:

(a) constructing a DNA construct comprising an integration cassette for integration of said DNA sequence of interest, said cassette being flanked by recombination sequences in which is inserted said DNA sequence of interest, wherein said DNA sequence of interest is flanked by a nucleotide sequence sharing homology with a genomic nucleotide sequence present in more than one copy in the eukaryotic zygote per haploid genome; and b) microinjecting said DNA construct into said eukaryotic zygote.

2. The method of claim 1, wherein said genomic nucleotide sequence present in more than one copy is a bovine satellite sequence.

3. A method of increasing the rate of production of fertile, transgenic eukaryotic zygotes having a DNA sequence of interest integrated at a predetermined naturally occurring genomic DNA sequence of the zygotes comprising:

a) constructing a DNA construct comprising an integration cassette for integration of said DNA sequence of interest, said cassette being flanked by recombination sequences in which is inserted said DNA sequence of interest, wherein said DNA sequence of interest is flanked by a nucleotide sequence sharing homology with a genomic nucleotide sequence present in more than one copy in the eukaryotic zygotes per haploid genome; and b) microinjecting said DNA construct into said eukaryotic zygotes;

wherein said rate is greater than a modification of a method comprising steps a) and b) wherein the modification is that the DNA sequence of interest is flanked by a nucleotide sequence of interest sharing homology with a genomic nucleotide sequence present in only one copy per haploid genome.

4. The method of claim 3, wherein said genomic nucleotide sequence present in more than one copy is a bovine satellite sequence.

5. A method of transforming a eukaryotic cell by insertion of a DNA sequence of interest into a predetermined naturally occurring repeated genomic DNA sequence of a cultured eukaryotic zygote comprising a) constructing a DNA construct comprising an integration cassette for integration of said DNA sequence of interest, said cassette being flanked by recombination sequences in which is inserted said DNA sequence of interest, wherein said DNA sequence of interest is flanked by a nucleotide sequence sharing homology with a genomic nucleotide sequence present in more than one copy in the eukaryotic zygote per haploid genome; and b) microinjecting said DNA construct into said eukaryotic zygote.

6. The method of claim 5, wherein said genomic nucleotide sequence present in more than one copy is a bovine satellite sequence.

* * * * *

```
                         SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide primer
             PIII-1"

(iii) HYPOTHETICAL: NO (iv) ANTI-SENSE: NO (xi) SEQUENCE DESCRIPTION: SEQ ID NO:1:

GGGTATCACG AGGCCGGAT                                                19

(2) INFORMATION FOR SEQ ID NO:2:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide primer
             pPIII-2"

(iii) HYPOTHETICAL: NO (xi) SEQUENCE DESCRIPTION: SEQ ID NO:2:

GGCACCTATC TCAGCGAT                                                 18

(2) INFORMATION FOR SEQ ID NO:3:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide primer
             pPIII-3"

(iii) HYPOTHETICAL: NO (xi) SEQUENCE DESCRIPTION: SEQ ID NO:3:

GGAGGACCGA AGGAGCT                                                  17

(2) INFORMATION FOR SEQ ID NO:4:

(i) SEQUENCE CHARACTERISTICS:
        (A) LENGTH: 22 base pairs
        (B) TYPE: nucleic acid
        (C) STRANDEDNESS: single
        (D) TOPOLOGY: linear
```

-continued

```
        (ii) MOLECULE TYPE: other nucleic acid
             (A) DESCRIPTION: /desc = "oligonucleotide primer Neo"

(iii) HYPOTHETICAL: NO (xi) SEQUENCE DESCRIPTION: SEQ ID NO:4:

CCGCCTGGGT GGAGAGGCTA TT                                                    22

(2) INFORMATION FOR SEQ ID NO:5:

(i) SEQUENCE CHARACTERISTICS:
             (A) LENGTH: 23 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "oligonucleotide primer BS"

(iii) HYPOTHETICAL: NO (xi) SEQUENCE DESCRIPTION: SEQ ID NO:5:

CCGTCATCGC AAGATGAAGC CCT                                                   23

(2) INFORMATION FOR SEQ ID NO:6:

(i) SEQUENCE CHARACTERISTICS:
             (A) LENGTH: 21 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "oligonucleotide primer
                 KC-1"

(iii) HYPOTHETICAL: NO (xi) SEQUENCE DESCRIPTION: SEQ ID NO:6:

CCTGCCCAAA TTCCTCAATG G                                                     21

(2) INFORMATION FOR SEQ ID NO:7:

(i) SEQUENCE CHARACTERISTICS:
             (A) LENGTH: 22 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "oligonucleotide primer
                 KC-2"

(iii) HYPOTHETICAL: NO (xi) SEQUENCE DESCRIPTION: SEQ ID NO:7:

CTGCGTTGTC TTCTTTGATG TC                                                    22
```